US009579444B2

(12) United States Patent
Strömberg

(10) Patent No.: US 9,579,444 B2
(45) Date of Patent: Feb. 28, 2017

(54) BLOOD COLLECTION SYSTEM AND METHOD

(71) Applicant: LenJam AB, Gothenburg (SE)

(72) Inventor: Lennart Strömberg, Saltsjobaden (SE)

(73) Assignee: LENJAM AB, Gothenburg (SE)

( * ) Notice: Subject to any disclaimer, the term of this patent is extended or adjusted under 35 U.S.C. 154(b) by 230 days.

(21) Appl. No.: 14/412,568

(22) PCT Filed: Jul. 2, 2013

(86) PCT No.: PCT/SE2013/050845
§ 371 (c)(1),
(2) Date: Jan. 2, 2015

(87) PCT Pub. No.: WO2014/007742
PCT Pub. Date: Jan. 9, 2014

(65) Prior Publication Data
US 2015/0157780 A1   Jun. 11, 2015

(30) Foreign Application Priority Data

Jul. 5, 2012 (SE) ...................................... 1250769

(51) Int. Cl.
A61M 1/36 (2006.01)
A61M 1/02 (2006.01)

(52) U.S. Cl.
CPC ........ *A61M 1/3607* (2014.02); *A61M 1/0218* (2014.02); *A61M 1/0231* (2014.02);
(Continued)

(58) Field of Classification Search
CPC .............. A61M 1/0218; A61M 1/0231; A61M 1/0272; A61M 1/3607; A61M 1/3609;
(Continued)

(56) References Cited

U.S. PATENT DOCUMENTS 4,086,924 A    5/1978  Latham, Jr.
4,582,598 A    4/1986  Bilstad et al.
(Continued)

FOREIGN PATENT DOCUMENTS

WO    WO-0114048 A1    3/2001
WO    WO-2007101064 A2    9/2007

OTHER PUBLICATIONS

International Search Report PCT/ISA/210 for International Application No. PCT/SE2013/050845 Dated Oct. 18, 2013.

*Primary Examiner* — John Kim
(74) *Attorney, Agent, or Firm* — Harness, Dickey & Pierce, P.L.C.

(57) ABSTRACT

A blood collection system comprises a suction unit (11), a hose arrangement (12) connected to the suction unit, means for aspirating blood and air through the suction unit and for pumping said blood and air through the hose arrangement, a flow sensing unit (14) for continuously sensing the blood flow through the hose arrangement, an anticoagulant additive dosing system (15) for continuously dosing an anticoagulant additive into the blood flowed through the hose arrangement in response to the continuously sensed blood flow, a mixing unit (16) for mixing the blood with the anticoagulant additive dosed into the blood, and a collection vessel (17) for collecting the mixed blood and anticoagulant additive. The means for aspirating and pumping the blood and air is a pump system (13) providing a known constant volume flow of the blood and air in the hose arrangement, the flow sensing unit (14) is arranged for continuously sensing the mass flow of blood through the hose arrangement by means of continuously measuring a parameter indicative of the weight of blood in a tubing section (14*a*), through which the blood is transported, and the anticoagulant additive dosing system comprises a control unit (15*d*) connected to the flow sensing unit and arranged for auto-
(Continued)

matically controlling the continuously dosing of an anticoagulant additive into the blood flowed through the hose arrangement in response to the continuously sensed mass flow of blood.

19 Claims, 3 Drawing Sheets

(52) U.S. Cl.
CPC ........ *A61M 1/0272* (2013.01); *A61M 1/3609* (2014.02); *A61M 1/3672* (2013.01); *A61M 2205/3379* (2013.01); *A61M 2205/3382* (2013.01); *A61M 2205/3386* (2013.01); *A61M 2205/3393* (2013.01); *A61M 2205/3396* (2013.01)

(58) Field of Classification Search
CPC ........ A61M 1/3672; A61M 2205/3379; A61M 2205/3382; A61M 2205/3386; A61M 2205/3393; A61M 2205/3396

See application file for complete search history.

(56) References Cited

U.S. PATENT DOCUMENTS

| | | | |
|---|---|---|---|
| 4,769,001 A | 9/1988 | Prince | |
| 5,387,204 A * | 2/1995 | Olsson | A61M 1/0007 604/118 |
| 5,411,472 A | 5/1995 | Steg, Jr. et al. | |
| 5,769,537 A * | 6/1998 | Stromberg | B01F 15/02 366/108 |
| 8,211,048 B2 | 7/2012 | Szamosfalvi et al. | |
| 2009/0221948 A1 | 9/2009 | Szamosfalvi et al. | |
| 2012/0265116 A1 | 10/2012 | Szamosfalvi et al. | |

* cited by examiner

BLOOD COLLECTION SYSTEM AND METHOD

CROSS-REFERENCE TO RELATED APPLICATIONS

This application is a national phase under 35 U.S.C. §371 of PCT International Application No. PCT/SE2013/050845 which has an International filing date of Jul. 2, 2013, which claims priority to Swedish patent application number SE 1250769-5, filed on Jul. 5, 2012; the entire contents of each of which are hereby incorporated by reference.

TECHNICAL FIELD

The present invention relates to blood collection systems and methods.

DESCRIPTION OF RELATED ART AND BACKGROUND

In the health services organizations worldwide blood for homologous transfusion has always been and still is in short supply. Considerable amounts are used for transfusions on different indications, e.g., in connection to surgery on humans as mentioned above and in veterinary praxis. Blood is an expensive product due to the costs for collecting, testing and storing the same and the administration of the precise handling of the same. At homologous blood transfusions there is a risk of transferring detrimental diseases such as hepatitis, HIV infections, and different tropical diseases among others.

As an attempt to avoid the risks with homologous blood replacement, autologous blood transfusion has been suggested. In one autologous blood transfusion technique, the patient's own blood is collected during surgery from his surgical wound for a following re-transfusion of the "whole blood" when the patient will best need it. However, blood leaving the vascular bed will also get in contact with injured tissues forming the surgical wound's walls. This contact will activate the blood's coagulation.

When blood is sucked through a tubing system from a surgical wound into a blood collector the activation process will continue unless the internal surface of the tubing is blood compatible or until this process is stopped by an anticoagulant, such as a sodium citrate solution. Furthermore, it can not be avoided that air is also sucked into the system together with the blood. In fact much larger volumes of air are sucked than volumes of blood in the majority of the cases. The result is that almost all blood will pass through the system mixed with air as foam or froth until it has been defoamed.

It is important that the activation process resulting in polymerization or clot formation (coagulation) is stopped as early and complete as possible during that the blood is collected. This can only be achieved if an anticoagulant is added and mixed to the entire blood portion as early as possible during the blood collecting process. It should be noticed that the blood-air interface is not a blood compatible surface.

Beside blood and air the collected material may also contain non-desired tissue fragments from the surgical wound (clots, tissue fragments, fat, bone particles, etc.). These materials will also activate the same coagulation system during the blood collection process until the said system has been stopped (inactivated) by the added anticoagulant.

WO 01/14048 discloses a blood collection system comprising suction means for aspirating blood, a defoaming unit for defoaming the aspirated blood by virtue of subjecting the fluid to a G-force other than the force of gravity, a measuring device for in situ measuring the flow of the defoamed blood, a dosing means for dosing an additive, such as sodium citrate, into the blood at the output of the defoaming unit in dependence of preferably proportional to, the measured flow of the blood, a mixing unit for mixing the blood with the additive by virtue of subjecting the blood and the additive to a G-force other than the force of gravity, and a recipient for collecting the mixed blood and additive. The measuring device is an optical device arranged for measuring the amount of blood and the velocity of said amount, wherein the velocity is measured by recording the amount of blood in a first and in a second one-dimensional cross section of the tubing, located at different positions along the flow direction, at various times, and by correlating the recordings.

SUMMARY

While the technique disclosed in WO 01/14048 seems to take all requirements and limitations into consideration, it has failed in disclosing a measuring device for measuring the flow of blood sufficiently reliably, sufficiently fast, and sufficiently accurately to be used together with the dosing means for dosing the sodium citrate into the blood. Too often the amount of sodium citrate will be too high or too low, and sometimes, the measuring device is not capable to determine a blood flow at all.

Therefore, it is an object of the invention to provide a blood collection system and a blood collection method, by which a correct amount of anticoagulant additive, such as e.g. sodium citrate, always can be added to the blood at an early stage during blood collection.

It is a further object of the invention to provide such blood collection system and method, by which the blood flow can be established reliably, fast, and accurately.

It is yet a further object of the invention to such blood collection system and method, which are robust, easy, fast and flexible to set up and use, of small size, reliable, and of low cost.

Various aspects of the invention are found in the appended patent claims.

In one aspect a blood collection system is provided, which comprises a suction unit, a hose arrangement connected to the suction unit, means for aspirating blood and air through the suction unit and for pumping said blood and air through the hose arrangement, a flow sensing unit for continuously sensing the blood flow through the hose arrangement, an anticoagulant additive dosing system for continuously dosing an anticoagulant additive into the blood flowed through the hose arrangement in response to the continuously sensed blood flow, a mixing unit for mixing the blood with the anticoagulant additive dosed into the blood, and a collection vessel for collecting the mixed blood and anticoagulant additive.

The means for aspirating and pumping the blood and air is a pump system providing a known constant volume flow of the blood and air in the hose arrangement, the flow sensing unit is arranged for continuously sensing the mass flow of blood through the hose arrangement by means of continuously measuring a parameter indicative of the weight of blood in a tubing section, through which the blood is transported, and the anticoagulant additive dosing system comprises a control unit connected to the flow sensing unit and arranged for automatically controlling the continuously dosing of an anticoagulant additive into the blood flowed through the hose arrangement in response to the continuously sensed mass flow of blood.

The tubing section may be pivotably suspended and the flow sensing unit may comprise a weight sensing arrangement for continuously sensing the parameter indicative of the weight of blood in the pivotably suspended tubing section. Further, the tubing section may have two open ends in fluid communication with the hose arrangement, wherein the tubing section can be pivotably suspended at an inner end thereof, which comprises the two open ends. Still further, the pivotably suspended tubing section may comprise a U-shaped tubing section.

The weight sensing arrangement may comprises a cantilever provided with at least one strain gauge wherein the pivotably suspended tubing section is resting on the cantilever, e.g., about halfway between the inner end of the tubing section and an outer end thereof. In one version, the weight sensing arrangement comprises four strain gauges connected in a bridge, wherein two of the strain gauges are mounted on an upper side of the cantilever and two of the strain gauges are mounted on a lower side of the cantilever.

In another aspect a blood collection method is provided, which comprises the steps of: pumping blood and air through a hose arrangement; continuously sensing the blood flow through the hose arrangement; continuously dosing an anticoagulant additive into the blood flowed through the hose arrangement in response to the continuously sensed blood flow; mixing the blood with the anticoagulant additive dosed into the blood; and collecting the mixed blood and anticoagulant additive in a collection vessel. The blood and air are pumped through the hose arrangement by means of a pump system providing a known constant volume flow of the blood and air in the hose arrangement. The mass flow of blood through the hose arrangement is continuously sensed by means of continuously measuring a parameter indicative of the weight of blood in a tubing section, through which the blood is transported. Finally, the continuously dosing of an anticoagulant additive into the blood flowed through the hose arrangement is controlled in response to the continuously sensed mass flow of blood.

Advantages of the aspects above include the following:

The blood collection system and method may prevent activation of the coagulation of blood, add automatically adequate amounts of anticoagulant additive to the collected blood concomitant with the collection independent on whether the blood is mixed with air in a foam or not, mix the anticoagulant additive instantaneously, defoam and filter the collected blood, not deteriorate the blood quality, and be easy to operate and cost-efficient.

Collected blood can be transferred to blood storage units/ traditional blood bags immediately ready for use or delayed re-transfusion.

Further, the blood collection system and method may collect blood from a surgical or trauma wound during surgery similar to traditional suction techniques, have high degree of reliability of operation, and possess high precision of the dosing of the anticoagulant additive. The dosing of anticoagulant additive cannot be disturbed by any accidental compressions in the hose arrangement through which the blood is pumped.

Yet further, the blood collection system is safe, movable, flexible, staff economizing, and well adapted to the user. It is not bulky and can be placed in operation theaters at a distance where the system will not intrude on the limited space close to the operation table. The use of it does not affect the common surgical routines, does not require any advanced training, or does not require any expanding of power resources existing in most operation theaters.

Typically, the blood collection system is provided as a two-part system comprising one disposable unit (consisting of hoses and possibly plastic bags and parts of the flow sensing unit) and one non-disposable unit, a console, into which the disposable unit is mounted fast and easily.

Further characteristics and advantages will be evident from the following detailed description given hereinafter and the accompanying FIGS. 1-4, which are given by way of illustration only, and shall thus not limit the scope of the present invention.

BRIEF DESCRIPTION OF THE DRAWINGS

FIG. 2b is a schematic side elevation view of the flow sensing unit of FIG. 2a.

Identical reference numerals are used throughout the Figures to denote identical or similar components, portions, details and the like of the various embodiments.

DETAILED DESCRIPTION

Figure 1:
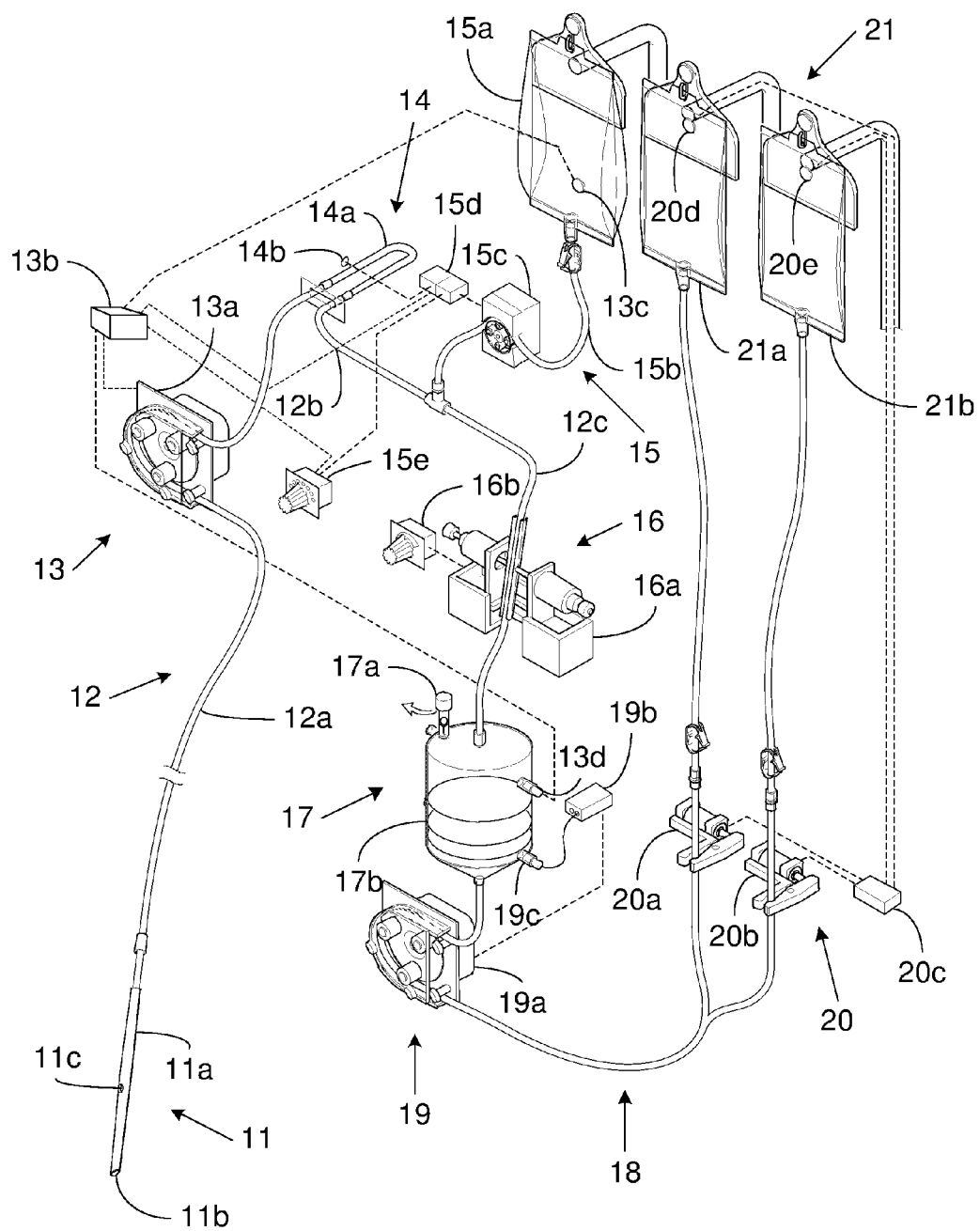
FIG. 1 is a schematic perspective view of a blood collection system according to one embodiment.

The blood collection system of FIG. 1 comprises a suction unit 11, a first hose arrangement 12, a first pump system 13, a flow sensing unit 14, an anticoagulant additive dosing system 15, a mixing and defoaming unit 16, and a filter unit or collection vessel 17. Optionally, the blood collection system also comprises a second hose arrangement 18, a second pump system 19, directing means, preferably a clamp arrangement 20, and a blood storage arrangement 21.

The suction unit 11 may comprise an elongated rigid, preferably transparent, tube 11a, e.g., made of plastic having an inlet end 11b and a hole (e.g. a no-return air valve unit) 11c, which can be covered by a finger tip during operation to concentrate all suction force to the inlet end 11b.

The first hose arrangement 12 may comprise three hose portions: a first portion 12a interconnecting the suction unit 11 and the flow sensing unit 14, a second portion 12b interconnecting the flow sensing unit 14 and the anticoagulant additive dosing system 15, and a third portion 12c interconnecting the anticoagulant additive dosing system 15 and the collection vessel 17. Each of the hose portions 12a-c may be made of a transparent flexible plastic.

The first pump system 13 may comprise a peristaltic or roller pump 13a, e.g., controlled by a control unit 13b, and may be arranged upstream of the flow sensing unit 14, and may thus be arranged to provide an under pressure in the suction unit 11 for aspirating blood and air through the inlet end 11b of the suction unit 11 and into the hose portion 12a and an over pressure downstream of the first pump system 13 for pumping blood and air through the hose portions 12a-c and into the collection vessel 17. The first pump system 13 is arranged to provide a known constant volume flow of the blood and air in the first hose arrangement 12. The blood and air is present as blood foam. When lifting the suction unit 11 from where the blood foam is aspirated, typically only air is sucked into the first hose arrangement 12.

The flow sensing unit 14 is arranged to continuously sense the mass flow of blood through the first hose arrangement 12 by means of continuously measuring a parameter indicative of the weight of blood in a tubing section 14a, through which the blood is transported by means of a weight sensing arrangement schematically indicated at 14b. Flow sensing units 14, which can be used with the blood collection system of FIG. 1, will be described in detail later with reference to FIGS. 2a-b and 3.

The anticoagulant additive dosing system 15 comprises a control unit 15d connected to the flow sensing unit 14, i.e. to the weight sensing arrangement 14b thereof, and is arranged to automatically control the continuously dosing of an anticoagulant additive into the blood flowed through the first hose arrangement 12 in response to the continuously sensed mass flow of blood. The anticoagulant additive dosing system 15 may thus comprise a storage unit 15a for the anticoagulant additive, a hose portion 15b interconnecting the anticoagulant additive storage unit 15a and the first hose arrangement 12 between the second and the third hose portions 12b-c. A pump, such as e.g. a peristaltic pump 15c, may be operatively connected to the hose portion 15b of the anticoagulant additive dosing system 15 in order to pump the anticoagulant additive into the blood flowed in the first hose arrangement 12 under control of the control unit 15d of the anticoagulant additive dosing system 15.

Further, The first pump system 13 and the anticoagulant additive dosing system 15 may be provided with an adjustment device 15e for manually adjusting the volume flow of the blood and air in the first hose arrangement 12 and consequently the dosing of the anticoagulant additive depending on the particular circumstances during operation, i.e. different suction forces may be desirable during operation.

The mixing and defoaming unit 16 is arranged to mix the blood with the anticoagulant additive dosed into the blood and may comprise a device 16a arranged to automatically move a portion of the third hose portion 12c back and forth, i.e. shaking the portion of the third hose portion 12c, which device 16a may be provided with an adjustment device 16b for manually adjusting an operation parameter such as shaking frequency or shaking amplitude. Typically, the mixing unit 16 is arranged to at least partly defoam the blood.

The filter unit or collection vessel 17 is arranged to collect the mixed blood and anticoagulant additive. It may comprise a valve 17a for letting air out and a filter arrangement 17b arranged to filter the mixed blood and anticoagulant collected in the collection vessel 17. The filter arrangement may comprise one or more filters arranged to separate foam, particles, bone residuals, eventually existing coagulum etc. Typically the filter arrangement may comprise three fabrics of different mesh size.

The second hose arrangement 18 may interconnect the collection vessel 17 and the blood storage arrangement 21, and the second pump system 19 may be arranged to pump the mixed blood and anticoagulant additive from the collection vessel 17 to the blood storage arrangement 21 by means of creating an under pressure in the collection vessel 17 to suck the mixed blood and anticoagulant additive from there and creating an over pressure downstream of the second pump system 19 to pump the mixed blood and anticoagulant additive to the blood storage arrangement 21.

The second pump system 19 may comprise a pump, e.g. a peristaltic pump 19a, and a control unit 19b arranged to control the second pump system 19.

The blood storage arrangement 21 may comprises a plurality of blood bags 21a-b connected in parallel via the second hose arrangement 18 and the clamp arrangement 20 may comprise clamps 20a-b connected to a control unit 20c for the control thereof, wherein the clamps 20a-b can be used to selectively direct the mixed and filtered blood and anticoagulant additive from the collection vessel 17 to a selected one of the blood bags 21a-b. It shall be appreciated that the blood storage arrangement 21 may comprise any number of blood collection units, such as blood bags, connected in parallel via the second hose arrangement 18 to the collection vessel 17. Similarly, the clamp arrangement 20 may comprise one clamp for each such parallel fluid path.

When a blood collection unit/blood bag is full it is exchanged for a new empty blood collection unit/blood bag. In such a manner any required number of blood collection units/blood bags can be filled by the blood collection system.

Figure 2A:
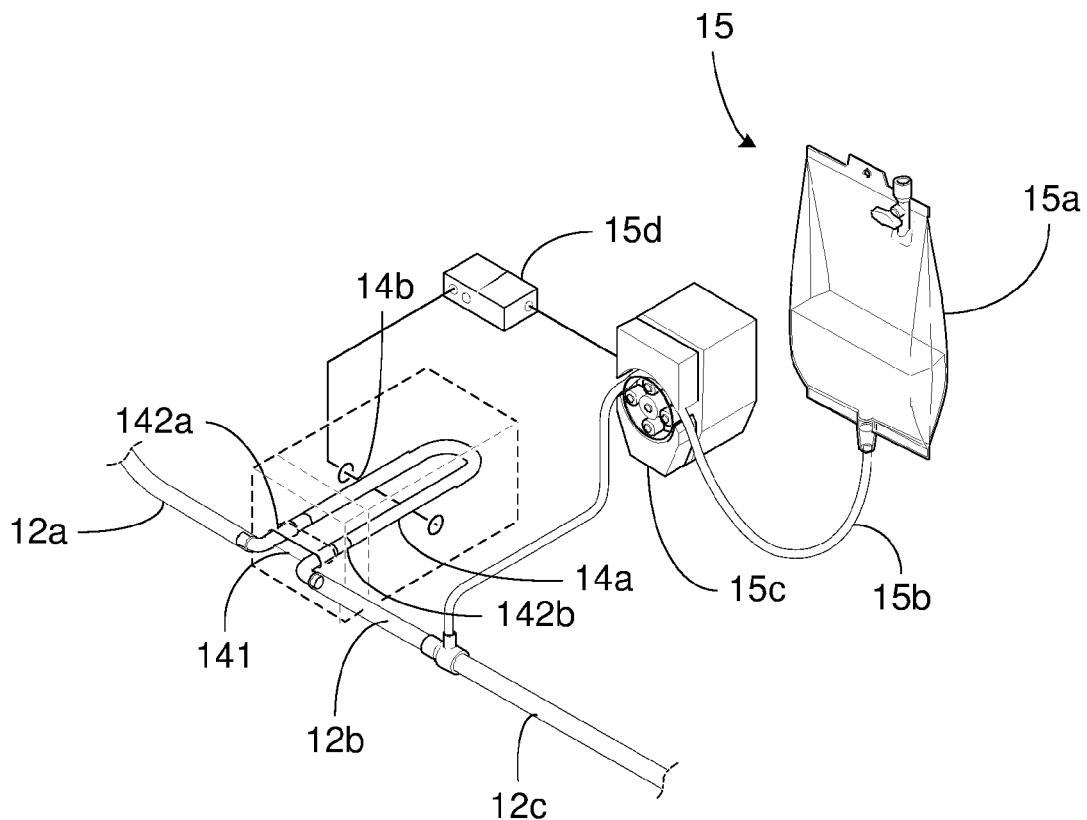
FIG. 2a is a schematic perspective view of a flow sensing unit and an anticoagulant additive dosing system which can be used with the blood collection system of FIG. 1.
Figure 2B:
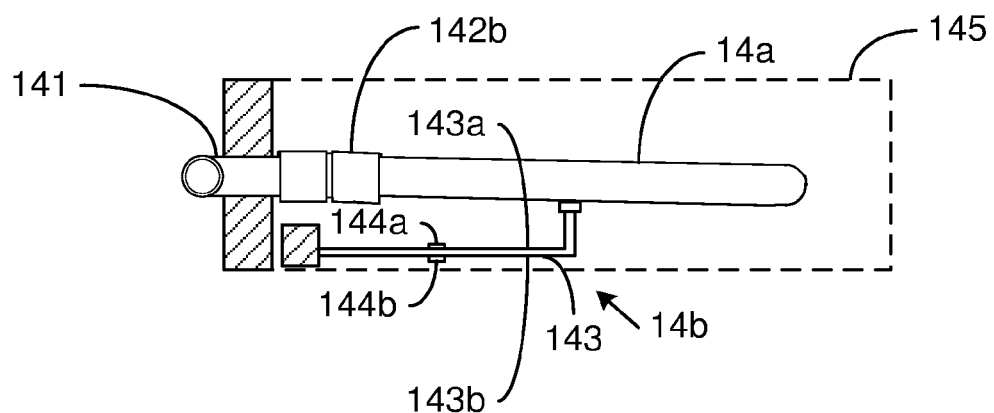
Figure 3:
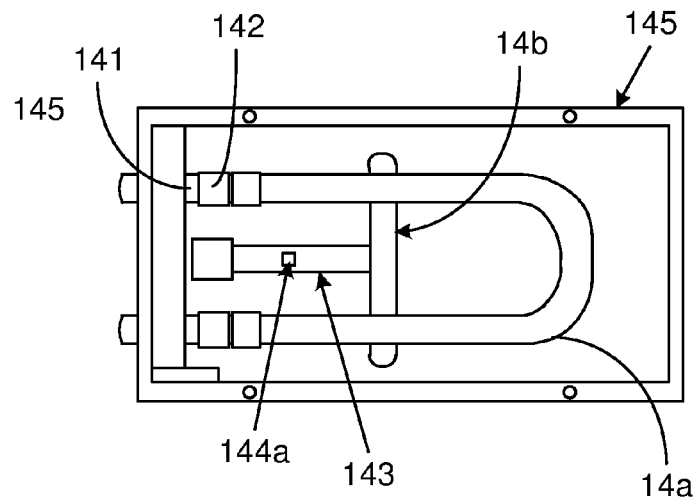
FIG. 3 is a schematic top view of a flow sensing unit which can be used with the blood collection system of FIG. 1.

With reference next to FIGS. 2a-b and 3, which are schematic perspective, side elevation, and top views, respectively, of a flow sensing unit which can be used with the blood collection system of FIG. 1. In FIG. 2a is also shown the anticoagulant additive dosing system 15 with its storage unit 15a, hose portion 15b, pump 15c, and control unit 15d.

The flow sensing unit may comprise a rigid base tubing section 141 which is connected to the first and second hose portions 12a-b of the first hose arrangement 12 and to the tubing section 14a, which may be essentially U-shaped, via flexible hose portions 142a-b. The U-shaped tubing section 14a, which is rigid, is thus pivotably suspended at 142a-b, i.e. at an inner end portion of the U-shaped tubing section 14a, and rests onto the weight sensing arrangement 14b schematically indicated in FIG. 2a. The flexible hose portions 142a-b may be made of a flexible plastic or rubber material.

The weight sensing arrangement 14b as seen in FIG. 2b comprises a cantilever 143 provided with at least one strain gauge 144a-b, wherein the pivotably tubing section 14a is resting on the cantilever 143. Preferably, the pivotably suspended tubing section 14a is resting on the cantilever 143 about halfway between the inner end of the U-shaped tubing and an outer end thereof. By such provisions, if the pivotably suspended tubing section is filled with a mix of blood and air, the entire weight of the blood is sensed (compared to only half the weight of the blood if the pivotably suspended tubing section 14a is resting on the cantilever 143 at the outer end thereof). A casing of the flow sensing unit 14 is denoted by 145.

In one embodiment, the weight sensing arrangement 14b comprises two strain gauges connected in a bridge, wherein one of the strain gauges are mounted on an upper side 143a of the cantilever and one of the strain gauges are mounted on a lower side 143b of the cantilever 143.

Typically, each of the strain gauges is mounted on the cantilever 143 close to where the cantilever 143 is attached.

In another embodiment, the weight sensing arrangement 14b comprises four strain gauges connected in a bridge, wherein two of the strain gauges are mounted on an upper side 143a of the cantilever and two of the strain gauges are mounted on a lower side 143b of the cantilever.

Figure 4:
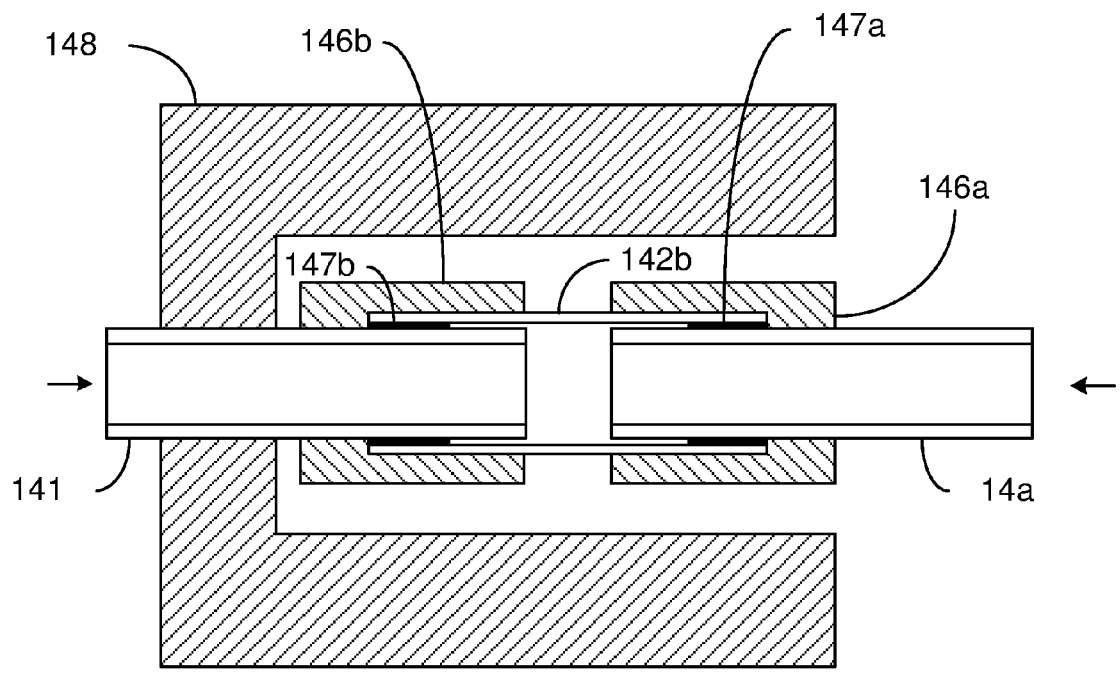
FIG. 4 is an enlarged schematic cross-sectional view of a part of a flow sensing unit which can be used with the blood collection system of FIG. 1.

FIG. 4 is an enlarged schematic cross-sectional view of a part of an alternative flow sensing unit which can be used with the blood collection system of FIG. 1.

The flow sensing unit may comprise a rigid base tubing section 141 which is connected to the first and second hose portions 12*a-b* of the first hose arrangement 12 and to the tubing section 14*a*, which may be essentially U-shaped, via flexible hose portions (only 142*b* shown in FIG. 4). The U-shaped tubing section 14*a*, which is rigid, is thus pivotably suspended at 142*a-b*, i.e. at an inner end portion of the U-shaped tubing section 14*a*, and rests onto a weight sensing arrangement (not illustrated). The flexible hose portions 142*b* may be made of a flexible plastic or rubber material.

The joints between each of the flexible hose portions 142*b* and the rigid base tubing section 141 and the U-shaped tubing section 14*a* may be formed as follows. The inner diameter of the flexible hose portions 142*b* is identical with or somewhat larger than the outer diameter of the rigid base tubing section 141 and the U-shaped tubing section 14*a*. Each joint is formed by an overlap between one of the flexible hose portions 142*b* and the rigid base tubing section 141 or the U-shaped tubing section 14*a*, in which overlap a glue line 147*a-b* is applied. In order to form a strong joint, a respective shrink hose portion 146*a-b* is threaded around the overlap and is treated, e.g. heated, to shrink and press against the overlap. A protection tubing 148 may be arranged around each of the flexible hose portions 142*b* at an appropriate distance in order to avoid explosion of any of the flexible hose portions 142*b* due to an over pressure within the flexible hose portion.

It is important that all parts coming into contact with blood are disposable parts or are easy to sterilize. This put restrictions on the design of the flow sensing unit. The above design enables the use of simple parts (the base tubing section 141, flexible hose portions 142*a-b*, and the pivotably suspended tubing section 14*a*) that can easily be exchanged, while the weight sensing arrangement 14*b* has no contact with the blood and thus not need to be exchanged for that reason.

All surfaces of part that risk to come in contact with blood such as e.g. the interior walls of the parts, i.e. the suction unit 11, the first hose arrangement 12, the base tubing section 141, flexible hose portions 142*a-b*, and the pivotably suspended tubing section 14*a* of the flow sensing unit 14, the collection vessel 17, the second hose arrangement and the blood bags 21*a-b* of the blood storage arrangement 21, should be blood compatible, i.e. made of or treated by a blood compatible material.

In one embodiment the interior walls of some or all of the above parts are heparinized or otherwise treated, e.g., as disclosed in U.S. Pat. No. 4,613,665, the contents of which being hereby incorporated by reference.

It shall further be appreciated that the blood collection system may be provided with a number of sensors, by which automatic safety operations can be performed.

The first pump system 13 may comprise a sensor 13*c* arranged to continuously sense whether a level of anticoagulant additive left in the anticoagulant additive dosing system 15 falls below a first threshold level, wherein the control unit 13*b* of the first pump system 13 can be arranged to automatically shut down the first pump system 13, i.e. stopping the pump 13*a* of the first pump system 13, in case the level of anticoagulant additive left in the anticoagulant additive dosing system 15 falls below the first threshold level. Hereby, under dosing of anticoagulant additive can be avoided. When the anticoagulant additive dosing system 15 runs short of of anticoagulant additive, the aspiration of blood is automatically halted.

Further, the control unit 13*b* of the first pump system 13 and the control unit 15*d* of the anticoagulant additive dosing system 15 may be connected to one another, wherein the control unit 13*b* of the first pump system 13 can be arranged to automatically inform the control unit 15*d* of the anticoagulant additive dosing system 15 when shutting down the first pump system 13, in response to which the control unit 15*d* of the anticoagulant additive dosing system 15 can be arranged to automatically stop the dosing of the anticoagulant additive into the blood flowed through the first hose arrangement 12. Hereby, over dosing of anticoagulant additive can be avoided. When the aspiration/pumping of blood through the first hose arrangement 12 is halted, the dosing of anticoagulant is automatically halted.

Further, the first pump system 13 may comprise a sensor 13*d* arranged to continuously sense whether a level of mixed blood and anticoagulant additive in the collection vessel 17 rises above a second threshold level, wherein the control unit 13*b* of the first pump system 13 can be arranged to automatically shut down the first pump system 13, i.e. stopping the pump 13*a* of the first pump system 13, in case the mixed blood and anticoagulant additive in the collection vessel rises above the second threshold level. Hereby, overflow of blood and anticoagulant additive in the blood collection system can be avoided. When the collection vessel 17 is close to become full, the aspiration of blood is automatically halted.

Yet further, the second pump system 19 may comprise a sensor 19*c* arranged to continuously sense whether a level of mixed blood and anticoagulant additive in the collection vessel 17 falls below a third threshold level, wherein the control unit 19*b* of the second pump system 19 can be arranged to automatically shut down the second pump system 19 in case the level of mixed blood and anticoagulant additive in the collection vessel 17 falls below the third threshold level. Hereby, it can be safeguarded that when the collection vessel 17 is close to become empty, the pumping by the second pump system 19 is automatically halted.

Still further, the clamp arrangement 20 may, for each of the blood bags 21*a-b*, comprise a sensor 20*d*, 20*e* arranged to continuously sense whether a level of mixed blood and anticoagulant additive in the blood bag 21*a-b* rises above a fourth threshold level, wherein the control unit 20*c* of the clamp arrangement 20 can be arranged to automatically control the clamps 20*a-b* such that mixed blood and anticoagulant additive from the collection vessel 17 is not directed to a blood bag 21*a-b* in case the level of mixed blood and anticoagulant additive in that blood bag 21*a-b* rises above the fourth threshold level. Hereby, it can be ensured that when each of the blood bags 21*a-b* becomes full, a respective clamp 20*a-b* closes the fluid communication between the collection vessel 17 and that blood bag 21*a-b*.

It shall be appreciated that the blood collection system may comprise less or more sensors, based on the sensing of which various actions may be taken. In such a manner an entirely automated blood collection system can be provided. Optionally, or alternatively, some or all of the sensors are connected to alarms, which may be triggered based on the sensing of the sensors.

It will be obvious that the invention may be varied in a plurality of ways within the scope of the appended patent claims.

The invention claimed is:

1. A blood collection system comprising a suction unit; a hose arrangement connected to said suction unit; means for aspirating blood and air through the suction unit and for pumping said blood and air through the hose arrangement; a flow sensing unit for continuously sensing the blood flow through the hose arrangement; an anticoagulant additive dosing system for continuously dosing an anticoagulant additive into said blood flowed through the hose arrangement in response to the continuously sensed blood flow; a mixing unit for mixing the blood with the anticoagulant additive dosed into the blood; and a collection vessel for collecting the mixed blood and anticoagulant additive, wherein
- said means for aspirating the blood and air through the suction unit and for pumping said blood and air through the hose arrangement is a pump system providing a known constant volume flow of the blood and air in said hose arrangement;
- the flow sensing unit is arranged for continuously sensing the mass flow of blood through the hose arrangement by means of continuously measuring a parameter indicative of the weight of blood in a tubing section, through which the blood is transported; and
- the anticoagulant additive dosing system comprises a control unit connected to the flow sensing unit and arranged for automatically controlling the continuously dosing of an anticoagulant additive into said blood flowed through the hose arrangement in response to the continuously sensed mass flow of blood characterized in that
- said tubing section has two open ends in fluid communication with the hose arrangement, the tubing section being pivotably suspended at an inner end thereof, which comprises the two open ends, and the flow sensing unit comprises a weight sensing arrangement for continuously sensing the parameter indicative of the weight of blood in said pivotably suspended tubing section.

2. The system of claim 1 wherein the pivotably suspended tubing section comprises a U-shaped tubing section.

3. The system of claim 1 wherein the weight sensing arrangement comprises a cantilever provided with at least one strain gauge wherein the pivotably suspended tubing section is resting on said cantilever.

4. The system of claim 3 wherein the pivotably suspended tubing section is resting on said cantilever about halfway between the inner end of the pivotably suspended tubing section and an outer end thereof.

5. The system of claim 3 wherein weight sensing arrangement comprises four strain gauges connected in a bridge, wherein two of the strain gauges are mounted on an upper side of the cantilever and two of the strain gauges are mounted on a lower side of said cantilever.

6. The system of claim 1 wherein the pump system comprises a peristaltic pump.

7. The system of claim 1 wherein
- the pump system comprises a control unit for controlling said pump system and a sensor for continuously sensing whether a level of anticoagulant additive left in said anticoagulant additive dosing system falls below a first threshold level; and
- the control unit of said pump system is arranged for automatically shutting down said pump system in case the level of anticoagulant additive left in said anticoagulant additive dosing system falls below said first threshold level.

8. The system of claim 7 wherein the control unit of said pump system and the control unit of the anticoagulant additive dosing system are connected to one another; and the control unit of said pump system is arranged for automatically informing the control unit of said anticoagulant additive dosing system when shutting down said pump system, wherein the control unit of said anticoagulant additive dosing system is arranged for automatically stopping the dosing of the anticoagulant additive into said blood flowed through the hose arrangement.

9. The system of claim 7 wherein the pump system comprises a sensor for continuously sensing whether a level of mixed blood and anticoagulant additive in said collection vessel rises above a second threshold level; and
- the control unit of said pump system is arranged for automatically shutting down said pump system in case the mixed blood and anticoagulant additive in said collection vessel rises above said second threshold level.

10. The system of claim 1 wherein the anticoagulant additive dosing system comprises a pump, preferably a peristaltic pump, connected to and controlled by the control unit of the anticoagulant additive dosing system.

11. The system of claim 1 wherein the collection vessel comprises a valve for letting air out and at least one filter arranged for filtering the mixed blood and anticoagulant collected in said collection vessel.

12. The system of claim 1 wherein said blood collection system further comprises a blood storage arrangement; a further hose arrangement interconnecting the collection vessel and the blood storage arrangement; and a further pump system arranged for pumping mixed blood and anticoagulant additive from the collection vessel to the blood storage arrangement.

13. The system of claim 12 wherein
- the further pump system comprises a control unit for controlling said further pump system and a sensor for continuously sensing whether a level of mixed blood and anticoagulant additive in said collection vessel falls below a third threshold level; and
- the control unit of said further pump system is arranged for automatically shutting down said further pump system in case the level of mixed blood and anticoagulant additive in said collection vessel falls below said third threshold level.

14. The system of claim 12 wherein the blood storage arrangement comprises a plurality of blood bags connected in parallel via the further hose arrangement; and said system further comprises means, preferably a clamp arrangement, arranged for selectively directing the mixed blood anticoagulant additive from the collection vessel to a selected one of the blood bags.

15. A blood collection method comprising the steps of: pumping blood and air through a hose arrangement; continuously sensing the blood flow through the hose arrangement; continuously dosing an anticoagulant additive into said blood flowed through the hose arrangement in response to the continuously sensed blood flow; mixing the blood with the anticoagulant additive dosed into the blood; and collecting the mixed blood and anticoagulant additive in a collection vessel, wherein
- the blood and air are pumped through the hose arrangement by means of a pump system providing a known constant volume flow of the blood and air in said hose arrangement;
- the mass flow of blood through the hose arrangement is continuously sensed by means of continuously measuring a parameter indicative of the weight of blood in a tubing section through which the blood is transported; and
- the continuously dosing of an anticoagulant additive into said blood flowed through the hose arrangement is controlled in response to the continuously sensed mass flow of blood characterized in that the mass flow of blood through the hose arrangement is continuously sensed by means of continuously measuring the parameter indicative of the weight of blood in a tubing section having two open ends in fluid communication with the hose arrangement, the tubing section being pivotably suspended at an inner end thereof, which comprises the two open ends.

16. The method of claim 15 wherein the mass flow of blood through the hose arrangement is continuously sensed by means of continuously measuring the parameter indicative of the weight of blood in a pivotably suspended tubing section comprising a U-shaped tubing section.

17. The method of claim 15 wherein the mass flow of blood through the hose arrangement is continuously sensed by means of continuously measuring the parameter indicative of the weight of blood in a pivotably suspended tubing section by means of at least one strain gauge arranged on a cantilever, on which the pivotably suspended tubing section is resting.

18. The method of claim 17 wherein the mass flow of blood through the hose arrangement is continuously sensed by means of continuously measuring the parameter indicative of the weight of blood in a pivotably suspended tubing section by means of at least one strain gauge arranged on a cantilever, on which the pivotably suspended tubing section is resting about halfway between the inner end of the U-shaped tubing and an outer end thereof.

19. The method of claim 17 wherein the mass flow of blood through the hose arrangement is continuously sensed by means of continuously measuring the parameter indicative of the weight of blood in a pivotably suspended tubing section by means of four strain gauges connected in a bridge, wherein two of the strain gauges are mounted on an upper side of the cantilever and two of the strain gauges are mounted on a lower side of said cantilever.

* * * * *